(12) United States Patent
Slone et al.

(10) Patent No.: US 9,034,049 B2
(45) Date of Patent: May 19, 2015

(54) EXTRA-ARTICULAR IMPLANTABLE MECHANICAL ENERGY ABSORBING ASSEMBLIES HAVING A TENSION MEMBER, AND METHODS

(71) Applicant: Moximed, Inc., Hayward, CA (US)

(72) Inventors: Clinton N. Slone, San Francisco, CA (US); Alan C. Regala, Seattle, WA (US); Joseph Luttwak, San Francisco, CA (US)

(73) Assignee: Moximed, Inc., Hayward, CA (US)

( * ) Notice: Subject to any disclaimer, the term of this patent is extended or adjusted under 35 U.S.C. 154(b) by 0 days.

(21) Appl. No.: 13/957,048

(22) Filed: Aug. 1, 2013

(65) Prior Publication Data

US 2013/0338783 A1 Dec. 19, 2013

Related U.S. Application Data

(62) Division of application No. 12/582,146, filed on Oct. 20, 2009, now Pat. No. 8,523,948.

(51) Int. Cl.
*A61F 2/30* (2006.01)
*A61F 2/38* (2006.01)
(Continued)

(52) U.S. Cl.
CPC ............... *A61F 2/3859* (2013.01); *A61B 17/56* (2013.01); *A61B 2017/00862* (2013.01); *A61B 2017/567* (2013.01); *A61F 2/38* (2013.01); *A61F 2/3836* (2013.01)

(58) Field of Classification Search
CPC ............... A61F 2002/30563; A61F 2002/0864
USPC ........................................... 623/18.11, 20.14
See application file for complete search history.

(56) References Cited

U.S. PATENT DOCUMENTS 2,267,848 A 12/1941 Talyor
3,242,922 A 3/1966 Thomas
(Continued)

FOREIGN PATENT DOCUMENTS

EP 0 383 419 A1 8/1990
WO WO 9406364 3/1994
(Continued)

OTHER PUBLICATIONS

Arendt, Anatomy and Malalignment of the Patellofemoral Joint. No. 436, pp. 71-75, 2005.
(Continued)

*Primary Examiner* — Bruce E Snow
*Assistant Examiner* — Brian Dukert
(74) *Attorney, Agent, or Firm* — Cermak Nakajima & McGowan LLP; Adam J. Cermak

(57) ABSTRACT

Implantable assemblies/devices and methods are provided for manipulating energy transferred by members defining an articulating anatomical joint, wherein the members collectively define a path of motion. Assemblies/devices are provided with a first component configured to be attached to a first anatomical member of the anatomical joint, a second component configured to be attached to a second anatomical member of the anatomical joint; and a tension member joining the first and second components. The tension member is placed under tension to absorb energy transferred by the anatomical members when the first component is attached to the first anatomical member and the second component is attached to the second anatomical member and a distance between locations of attachment of the first and second components becomes smaller then an implant-defined distance between the locations.

12 Claims, 12 Drawing Sheets

(51) Int. Cl.
*A61B 17/56* (2006.01)
*A61B 17/00* (2006.01)

(56) References Cited

U.S. PATENT DOCUMENTS

| | | |
|---|---|---|
| 3,648,294 A | 3/1972 | Shahrestani |
| 3,928,872 A | 12/1975 | Johnson |
| 4,100,918 A | 7/1978 | Glancy |
| 4,187,841 A | 2/1980 | Knutson |
| 4,246,660 A | 1/1981 | Wevers |
| 4,308,863 A | 1/1982 | Fischer |
| 4,433,679 A | 2/1984 | Mauldin et al. |
| 4,501,266 A | 2/1985 | McDaniel |
| 4,570,625 A | 2/1986 | Harris et al. |
| 4,576,158 A | 3/1986 | Boland |
| 4,621,627 A | 11/1986 | DeBstiani et al. |
| 4,637,382 A | 1/1987 | Walker et al. |
| 4,696,293 A | 9/1987 | Ciullo |
| 4,873,967 A | 10/1989 | Sutherland |
| 4,988,349 A | 1/1991 | Penning |
| 5,019,077 A | 5/1991 | Bastiani et al. |
| 5,026,372 A | 6/1991 | Sturtzkoph et al. |
| 5,041,112 A | 8/1991 | Mingozzi et al. |
| 5,063,916 A | 11/1991 | France et al. |
| 5,103,811 A | 4/1992 | Crupi, Jr. |
| 5,152,280 A | 10/1992 | Danieli |
| 5,375,823 A | 12/1994 | Navas et al. |
| 5,405,347 A | 4/1995 | Lee et al. |
| 5,578,038 A | 11/1996 | Slocum |
| 5,624,440 A | 4/1997 | Huebner |
| 5,658,241 A | 8/1997 | Deharde et al. |
| 5,662,648 A | 9/1997 | Faccioli et al. |
| 5,662,650 A | 9/1997 | Bailey et al. |
| 5,672,175 A | 9/1997 | Martin |
| 5,681,313 A | 10/1997 | Diez |
| 5,685,830 A | 11/1997 | Bonutti |
| 5,695,496 A | 12/1997 | Orsak et al. |
| 5,728,172 A | 3/1998 | Krieger |
| 5,803,924 A | 9/1998 | Oni et al. |
| 5,823,931 A | 10/1998 | Gilmour |
| 5,873,843 A | 2/1999 | Draper |
| 5,976,125 A | 11/1999 | Graham et al. |
| 5,976,136 A | 11/1999 | Bailey et al. |
| 6,010,474 A | 1/2000 | Wycoki |
| 6,013,103 A | 1/2000 | Kaufman et al. |
| 6,036,691 A | 3/2000 | Richardson et al. |
| 6,162,223 A | 12/2000 | Orsak et al. |
| 6,176,860 B1 | 1/2001 | Howard |
| 6,264,696 B1 | 7/2001 | Reigner et al. |
| 6,277,124 B1 | 8/2001 | Haag |
| 6,471,664 B1 | 10/2002 | Campbell et al. |
| 6,494,914 B2 | 12/2002 | Brown et al. |
| 6,527,733 B1 | 3/2003 | Ceriani et al. |
| 6,540,708 B1 | 4/2003 | Manspeizer |
| 6,599,322 B1 | 7/2003 | Amrich et al. |
| 6,620,332 B2 | 9/2003 | Amrich |
| 6,752,775 B2 | 6/2004 | Seligman et al. |
| 6,764,457 B2 | 7/2004 | Hogg |
| 6,875,235 B2 | 4/2005 | Ferree |
| 6,972,020 B1 | 12/2005 | Grayson et al. |
| 7,018,418 B2 | 3/2006 | Amrich et al. |
| 7,029,475 B2 | 4/2006 | Panjabi |
| 7,150,721 B2 | 12/2006 | Houser et al. |
| 7,188,626 B2 | 3/2007 | Foley et al. |
| 7,201,728 B2 | 4/2007 | Sterling |
| 7,235,102 B2 | 6/2007 | Ferree et al. |
| 7,241,298 B2 | 7/2007 | Nemec et al. |
| 7,247,157 B2 | 7/2007 | Prager et al. |
| 7,291,171 B2 | 11/2007 | Ferree |
| 7,393,335 B2 | 7/2008 | Carvey et al. |
| 2002/0052568 A1 | 5/2002 | Houser et al. |
| 2002/0068979 A1 | 6/2002 | Brown et al. |
| 2003/0109817 A1 | 6/2003 | Berl |
| 2003/0149386 A1 | 8/2003 | Ceriani et al. |
| 2004/0153015 A1 | 8/2004 | Seligman et al. |
| 2004/0260302 A1 | 12/2004 | Manspeizer |
| 2004/0267179 A1 | 12/2004 | Lerman |
| 2005/0049708 A1* | 3/2005 | Atkinson et al. ........... 623/17.16 |
| 2005/0055025 A1 | 3/2005 | Zacouto et al. |
| 2005/0251080 A1 | 11/2005 | Hyde, Jr. |
| 2005/0261680 A1 | 11/2005 | Draper |
| 2006/0064169 A1 | 3/2006 | Ferree |
| 2006/0094989 A1 | 5/2006 | Scott et al. |
| 2006/0116616 A1 | 6/2006 | Albrecht et al. |
| 2006/0142680 A1 | 6/2006 | Iarocci |
| 2006/0241640 A1 | 10/2006 | Briard et al. |
| 2007/0053963 A1 | 3/2007 | Hotchkiss |
| 2007/0106299 A1 | 5/2007 | Manspeizer |
| 2007/0168033 A1 | 7/2007 | Kim et al. |
| 2007/0244488 A1 | 10/2007 | Metzger et al. |
| 2008/0044449 A1 | 2/2008 | McKay |
| 2008/0275560 A1 | 11/2008 | Clifford et al. |
| 2008/0275561 A1 | 11/2008 | Clifford et al. |
| 2008/0275562 A1 | 11/2008 | Clifford et al. |
| 2008/0306324 A1 | 12/2008 | Bonutti et al. |
| 2009/0014016 A1 | 1/2009 | Clifford et al. |
| 2009/0018665 A1 | 1/2009 | Clifford et al. |

FOREIGN PATENT DOCUMENTS

| | | |
|---|---|---|
| WO | WO 9619944 | 7/1996 |
| WO | WO 02078554 A1 | 10/2002 |
| WO | WO 2004024037 A1 | 3/2004 |
| WO | WO2006/020530 A2 | 2/2006 |
| WO | WO 2007117571 A2 | 10/2007 |

OTHER PUBLICATIONS

Andriacchi, et al., Methods for evaluating the progression of osteoarthritis. No. 2, vol. 37, pp. 163-170, 2000.

Articular Cartilage, Degenerative Process, and Repair: Current Progress. pp. 738-744, 2006.

Deie, et al., A New Articulated Distraction Arthroplasty Device for Treatment of the Osteoarthritic Knee Joint: A Preliminary Report. vol. 23, No. 8, pp. 833-838, 2007.

Gunther., Surgical Approaches for Osteoarthritis. vol. 15, No. 4, pp. 627-643, 2001.

Joint Distraction for Osteoarthirtis. vol. 347, pp. 279-280, 1996.

Leon, et al. Minimally Invasive Selective Osteotomy of the Knee: A New Surgical Technique. vol. 17, No. 5, pp. 510-516, 2001.

Pollo, et al., Reduction of Medial Compartment Loads with Valgus Bracing of the Osteorthritic Knee. vol. 30, No. 3, pp. 414-421, 2002.

Repicci, et al , Minimally invasive unicondylar knee arthroplasty for the treatment of unicompartmental osteoarthritis: an outpatient arthritic bypass procedure. pp. 201-216, 2004.

Sharma, et al., The Role of Knee Alignment in Disease Progression and Functional Decline in Knee Osteoarthritis. vol. 286, No. 2, pp. 188-194, 2006.

Esch, et al., Structural joint changes, malalignment, and laxity in osteoarthritis of the knee. pp. 298-301, 34, 2005.

Sharma et al., The Mechanism of the Effect of Obesity in Knee Osteoarthritis. vol. 43, No. 3, pp. 568-575. 2000.

V-VAS a new concept in unloader knee orthosis design. pp. 1-4, 2006.

Supplementary European Search Report for European Patent App. No. 10825424.4 (Feb. 12, 2015).

* cited by examiner

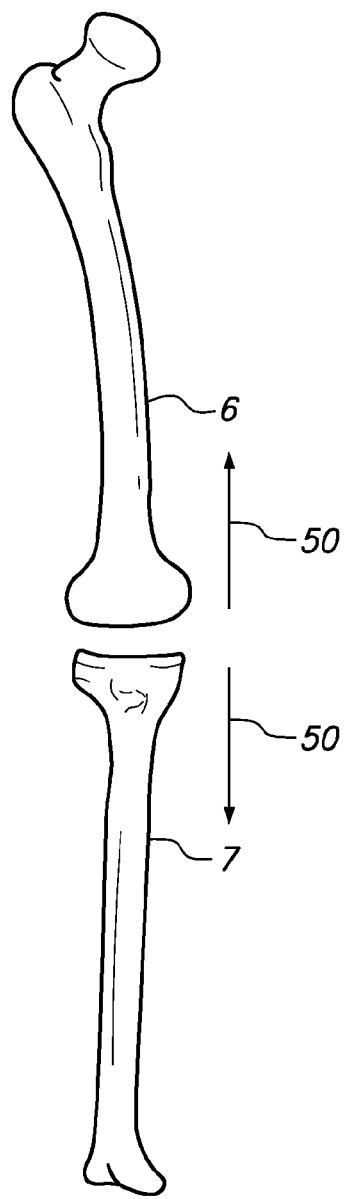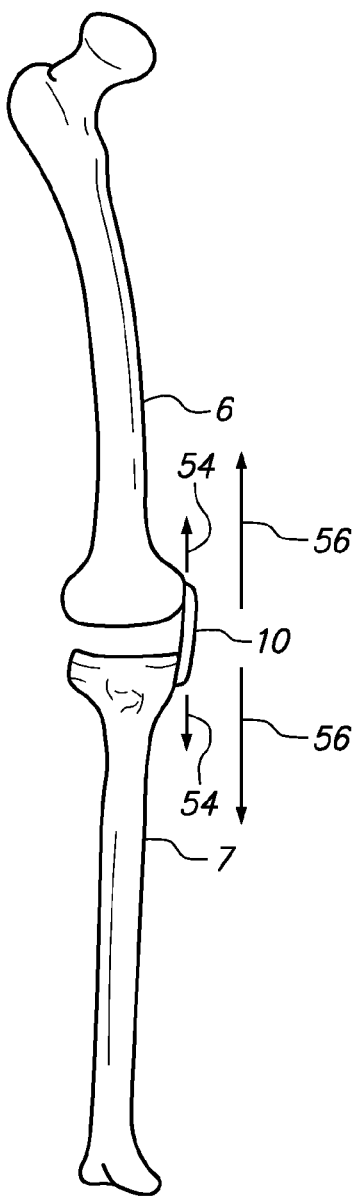

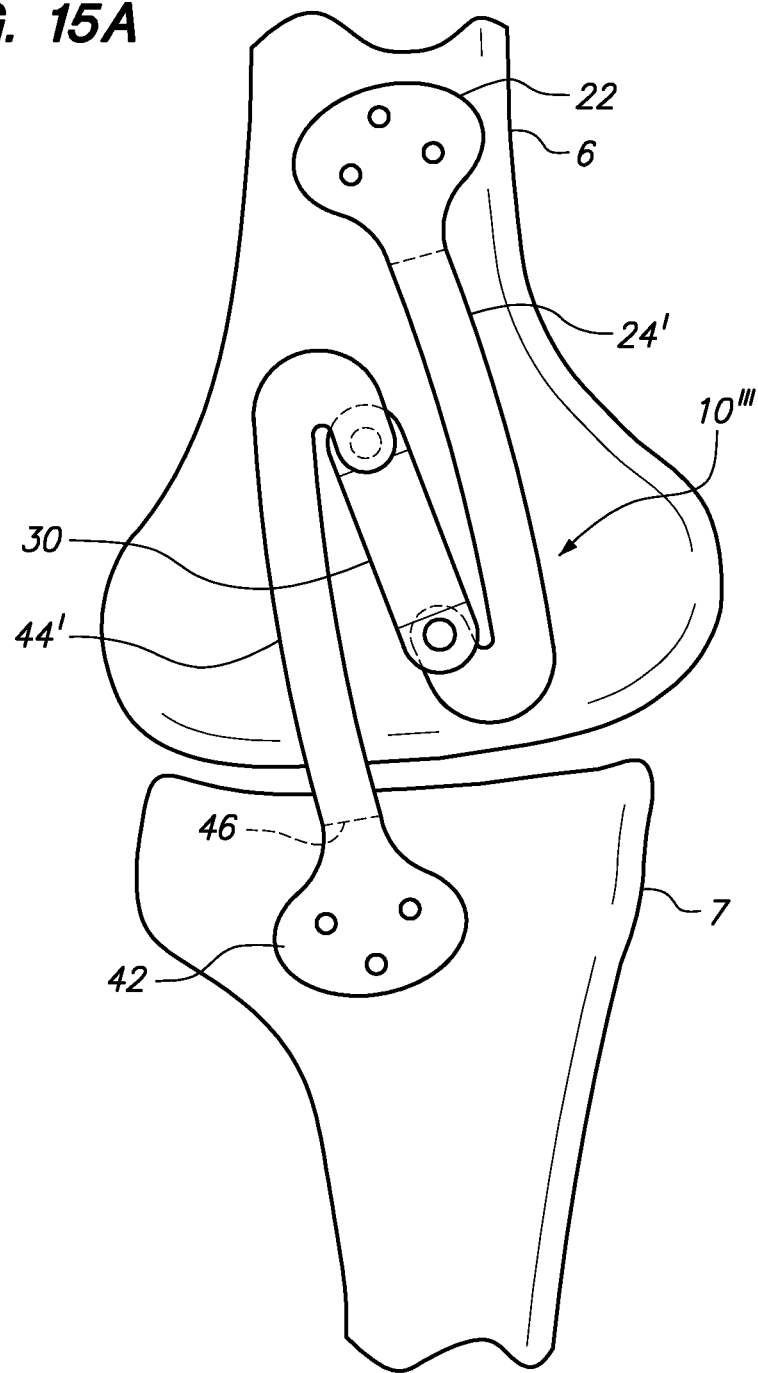

EXTRA-ARTICULAR IMPLANTABLE MECHANICAL ENERGY ABSORBING ASSEMBLIES HAVING A TENSION MEMBER, AND METHODS

This application is a divisional of U.S. application Ser. No. 12/582,146, filed Oct. 20, 2009, the contents of which are incorporated by reference.

FIELD OF THE INVENTION

The present invention is directed towards systems and methods for treating tissue of a body and more particularly, towards approaches designed to reduce mechanical energy transferred between members forming a natural joint.

BACKGROUND OF THE INVENTION

A joint is the location at which two or more bones make contact. The are constructed to allow movement and provide mechanical support, and are classified structurally and functionally. Structural classification is determined by how the bones connect to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/immovable bones are connected by dense connective tissue, consisting mainly of collagen. The fibrous joints are fluffier divided into three types:
  sutures which are found between bones of the skull;
  syndesmosis which are found between long bones of the body; and
  gomphosis which is a joint between the root of a tooth and the sockets in the maxilla or mandible.

Cartilaginous bones are connected entirely by cartilage (also known as "synchondroses"). Cartilaginous joints allow more movement between bones than to fibrous joint but less than the highly mobile synovial joint. An example of a cartilaginous joint is an intervertebral disc. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. hinge—such as the elbow; 3. pivot—such as the radius and ulna; 4. condyloidal (or ellipsoidal)—such as the wrist between radius and carps, or knee; 5. saddle—such as the joint between carpal thumbs and metacarpals; and 6. gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibrocartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Cartilage is a type of dense connective tissue and as noted above, it forms a critical pan of the functionality of a body joint. It is composed of collagenous fibers and/or elastin fibers, and cells called chondrocytes, all of which are embedded in a firm gel-like ground substance called the matrix. Articular cartilage is avascular (contains no blood vessels) and nutrients are diffused through the matrix. Cartilage serves several functions, including providing a framework upon which bone deposition can begin and supplying smooth surfaces for the movement of articulating bones. Cartilage is found in many places in the body including the joints, the rib cage, the ear, the nose, the bronchial tubes and between intervertebral discs. There are three main types of cartilage: hyaline, elastic and fibrocartilage.

Chondrocytes are the only cells found in cartilage. They produce and maintain the cartilaginous matrix. Experimental evidence indicates that cells are sensitive to their mechanical (stress-strain) state, and react directly to mechanical stimuli. The biosynthetic response of chondrocytes was found to be sensitive to the frequency and amplitude of loading (Wong et al., 1999 and Kurz et al., 2001). Recent experimental studies further indicate that excessive, repetitive loading may induce cell death, and cause morphological and cellular damage, as seen in degenerative joint disease (Lucchinetti et al., 2002 and Sauerland et al., 2003). Islam et al. (2002) found that continuous cyclic hydrostatic pressure (5 MPa, 1 Hz for 4 hours) induced apoptosis in human chondrocytes derived from osteoarthritic cartilage in vitro. In contrast, cyclic, physiological-like loading was found to trigger a partial recovery of morphological and ultra-structural aspects in osteoarthritic human articular chondrocytes (Nerucci et al., 1999).

Cancellous bone (also known as trabecular, or spongy) is a type of osseous tissue which also forms an important aspect of a body joint. Cancellous bone has a low density and strength but very high surface area, that fills the inner cavity of long bones. The external layer of cancellous bone contains red bone marrow where the production of blood cellular components (known as hematopoiesis) takes place. Cancellous bone is also where most of the arteries and veins of bone organs are found. The second type of osseous tissue is known as cortical bone, forming the hard outer layer of bone organs.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis is chronic pain, causing loss of mobility and often stiffness. "Pain" is generally described as a sharp ache, or a burning sensation in the associated muscles and tendons. OA can cause as crackling noise (called "crepitus") when the affected joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used and loaded throughout the day, thus distinguishing it from rheumatoid arthritis. With progression in OA, cartilage loses its viscoelastic properties and its ability to absorb load.

Generally speaking, the process of clinically detectable osteoarthritis is irreversible, and typical treatment consists of medication or other interventions that can reduce the pain of OA and thereby improve the function of the joint. According to an article entitled "Surgical approaches for osteoarthritis" by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodeses.

Arthrodeses are described as being reasonable alternatives for treating OA of small hand and foot joints as well as degenerative disorders of the spine, but were deemed to be rarely indicated in large weight-bearing joints such as the knee due to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. Thus, the correction of mechanical abnormalities by osteotomy and joint debridement are still considered as treatment options in many patients. Moreover, patients with limb malalignment, instability and intra-articular causes of mechanical dysfunction can benefit from an osteotomy to provide pain relief, with the goal being the transfer of weight-bearing forces from arthritic portions to healthier locations of a joint.

Joint replacement is one of the most common and successful operations in modern orthopedic surgery. It of replacing painful, arthritic, worn or diseased parts of the joint with artificial surfaces shaped in such a way as to allow joint movement. Such procedures are a last resort treatment as they are highly invasive and require substantial periods of recovery. Some forms of joint replacement are referred to as total joint replacement indicating that all joint surfaces are replaced. This contrasts with hemiarthroplasty (half arthroplasty) in which only one bone's joint surface is replaced and unicompartmental arthroplasty in which both surfaces of the knee, for example, are replaced but only on the inner or outer sides, not both. Thus, arthroplasty, as a general term, is an operative procedure of orthopedic surgery performed, in which the arthritic or dysfunctional joint surface is replaced with something better or by remodeling or realigning the joint by osteotomy or some other procedure. These procedures are also characterized by relatively long recovery times and are highly invasive procedures. The currently available therapies are not condro-protective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc. Osteotomy to restore or modify joint congruity is also an arthroplasty.

Osteotomy is a related surgical procedure involving cutting of bone to improve alignment. The goal of osteotomy is to relieve pain by equalizing forces across the joint as well as increase the lifespan of the joint. This procedure is often used in younger, more active or heavier patients. High tibial osteotomy (HTO) is associated with a decrease in pain and improved function. However, HTO does not address ligamentous instability—only mechanical alignment. HTO is associated with good early results, but results typically deteriorate over time.

Other approaches to treating osteoarthritis involve an analysis of loads that exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on a joint undergoing treatment or therapy, to thereby enable use of the joint within a healthy loading zone.

Certain other approaches to treating osteoarthritis contemplate external devices such as braces or fixators which control the motion of the bones at a joint or apply cross-loads at a joint to shift load from one side of the joint to the other. Various of these approaches have had some success in alleviating pain but suffer from patient compliance or lack an ability to facilitate and support the natural motion and unction of the diseased joint. Notably, the motion of bones thrilling a joint can be as distinctive as a finger print, and thus, each individual has his or her own unique set of problems to address. Therefore, mechanical approaches to treating osteoarthritis have had limited applications.

Prior approaches to treating osteoarthritis have also been remiss in acknowledging all of the basic functions of the various structures of a joint in combination with its unique movement. That is, in addition to addressing loads at a joint and joint movement, there has not been an approach which also acknowledges the dampening and energy absorption functions of the anatomy, and taking a minimally invasive approach in implementing solutions. Prior devices designed to reduce the load transferred by the natural joint typically describe rigid body systems that are incompressible. Mechanical energy is the product of force (F) and displacement distance(s) of a given mass (i.e., E=Fxs, for a given mass M). These systems have zero displacement within their working body (s=0). Since there is no displacement within the device it is reasonable to say that there is no energy storage or absorption in the device. Such devices act to transfer and not absorb energy from the joint. By contrast the natural joint is not a rigid body but is comprised of elements of different compliance characteristics such as bone, cartilage, synovial fluid, muscles, tendons, ligaments, etc as described above. These dynamic elements act to both transfer and absorb energy about the joint. For example cartilage compresses under applied force and therefore the resultant force displacement product represents the energy absorbed by cartilage. In addition cartilage has a non linear force displacement behavior and is considered viscoelastic. Such systems not only absorb and store, but additionally act to dissipate energy.

Therefore, approaches to treating joint pain are needed that address both joint movement and varying loads as well as energy absorption provided by an articulating joint.

The present invention satisfies these and other needs.

SUMMARY OF THE INVENTION

The present invention provided implantable assemblies having a tension member and configured for transiently absorbing load that is otherwise transferred from a first anatomical member to a second anatomical member of an articulating anatomical joint when the assembly is not installed thereto. Methods of implanting such assemblies are also provided.

An implant assembly is provided, comprising: a first component configured to be attached to a first anatomical member of an articulating, anatomical joint; a second component configured to be attached to a second anatomical member of the anatomical joint; and a tension member joining the first and second components; wherein the tension member is placed under tension to transiently, variably reduce load transferred from the first anatomical member to the second anatomical member when the first component is attached to the first anatomical member and the second component is attached to the second anatomical member and a distance between locations of attachment of the tension member to the first and second components becomes smaller then an implant-defined distance between the locations, and wherein the tension in the tension member decreases as the anatomical joint moves from extension to flexion.

In at least one embodiment, end portions of the first and second components joined by the tension member substantially overlap in an orientation configured to be assumed when the anatomical joint is in extension.

In at least one embodiment, end portions of the first and second components joined by the tension member are curved and do not overlap in an orientation configured to be assumed when the anatomical joint is in extension, and when viewed in a direction normal to a plane that is tangent to a location of attachment of at least one of said first and second components to the first and second anatomical members, respectively.

In at least one embodiment, end portions of the first and second components cross one another in a scissoring action upon movement from a configuration to be assumed when the anatomical joint is in extension to a configuration to be assumed when the anatomical joint is in flexion.

In at least one embodiment, a pivot point location on the first component relative to the second component remains substantially the same over the course of a range of motion from extension to flexion.

In at least one embodiment, a pivot point location on the first component relative to the second component shifts slightly over the course of a range of motion from extension to flexion to reduce an amount of load reduction by the tension member as the pivot point location shifts.

In at least one embodiment, a pivot point location on the first and second components substantially overlies a location on the anatomical joint that approximates the axis of rotation of the anatomical joint.

In at least one embodiment, the tension member comprises an elastomer.

In at least one embodiment, the tension member comprises a spring.

In at least one embodiment, at least one of the first and second components is connected to the tension member in a manner that prevents relative translation therebetween, but permits relative rotation therebetween.

In at least one embodiment, one of the first and second components is connected to the tension member in a manner that prevents relative translation therebetween and prevents relative rotation therebetween.

In at least one embodiment, the tension member permits relative axial rotations between the first and second components.

In at least one embodiment, the anatomical joint is a knee joint, the first component is adapted to be fixed to a femur of the knee joint and second component is adapted to be fixed to a tibia of the knee joint.

In at least one embodiment, the tension member extends and absorbs energy from the forces applied by the members of the anatomical joint, thereby relieving at least a portion of the load resultant from the forces from being transferred through contacting surfaces of the anatomical joint.

In at least one embodiment, the assembly relieves load on a side of the anatomical joint to which the assembly is attached.

A method for treating an articulating anatomical joint is provided, including: attaching a first component of an assembly to a first anatomical member of the anatomical joint; and attaching a second component of the assembly to a second anatomical member of the anatomical joint; wherein a tension member joins the first and second components to absorb load between the first and second members of the anatomical joint, and wherein the tension in the tension member decreases as the anatomical joint moves from extension to flexion.

In at least one embodiment, the tension member transiently absorbs the load.

In at least one embodiment, at least a limited amount of axial rotation is permitted between the first and second members of the anatomical joint.

In at least one embodiment, the tension member extends in directions substantially opposite to directions of load applied by the first and second members of the anatomical joint toward one another.

In at least one embodiment, the first and second components are attached at locations to place the first and second components where they intersect about a pivoting location to perform a scissoring action during movement of the anatomical joint.

In at least one embodiment, the anatomical joint is a knee joint, and the location is about the midpoint of a Blumensaat's line of a femur of the knee joint.

These and other features of the invention will become apparent to those persons skilled in the art upon reading the details of the assemblies and methods as more fully described below.

BRIEF DESCRIPTION OF THE DRAWINGS

FIG. 1 is a front view, illustrating normal forces existing in a joint.

FIG. 2 is a front view, depicting the effect an energy manipulating assembly of the present invention has on the joint shown in FIG. 1.

FIG. 15A is a medial side view of another embodiment of an assembly installed on a knee joint according to the present invention.

DETAILED DESCRIPTION OF THE INVENTION

Figure 3:
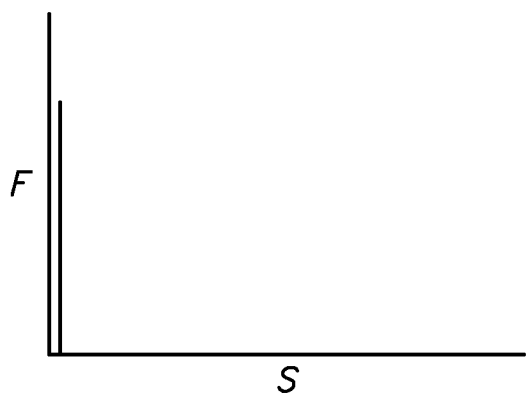
FIG. 3 is a graph of force versus displacement, illustrating the energy characteristics of a prior art rigid structure applied across a joint.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Referring now to the drawings, which are provided by way of example and not limitation, the present invention is directed towards devices and methods for treating body tissues. In applications relating to the treatment of body joints, the present invention seeks to alleviate pain associated with the function of diseased, overloaded or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee and shoulder, as well as other synovial or articular cartilaginous joints of the body such as those of the hips, fingers, wrists, ankles and toes. However, it is also contemplated that the apparatus and method of the present invention can be employed to treat other, non-synovial, non-articular non-cartilaginous joints that are capable of motion in a flexion/extension direction that exceeds forty-five degrees.

In one particular aspect, the extra articular energy absorbing assemblies of the present invention seek to permit and complement the unique articulating motion of a body joint of a patient while simultaneously manipulating energy being experienced by both cartilage and osseous tissue (cancellous and cortical bone). To minimize pain, transient variable load reduction or absorption of 1-40% of forces, in varying degrees, may be necessary. Transient variable load reduction or absorption in the range of 5-30% can be a target for certain applications. Transient variable load reduction or absorption refers to the function of the energy absorbing or manipulation structure reducing the load experienced by the joint during the joint's higher load positions and the energy manipulation structure not reducing the load experienced by the joint during the joints lower or no load positions. In certain specific applications, transient distraction is employed in the energy manipulation approach.

In order to implant the extra articular energy absorbing assemblies of the present invention, conventional surgical or minimally invasive surgical approaches are used to gain access to a body joint or other anatomy requiring attention. Arthroscopic approaches are contemplated when reasonable to both implant the energy manipulation assembly as well as to accomplish adjusting an implanted assembly. Biologically inert materials of various kinds can be employed in constructing the energy manipulation assemblies of the present invention.

In one particular approach, an extra articular energy absorbing device is provided including a tension member used as the energy absorber. The tension member is deformed to manipulate or absorb threes/load between body parts that are joined at a body joint, to which body parts the device is mounted. The tension member is used in a novel way in the present invention to control the manner in which two bones of a joint move toward one another. The tension member is also used in a novel way in the present invention to provide less resistance as the joint goes through greater angles of flexion (lower load positions), rather than preventing the joint from flexing. The energy absorbing assemblies as described herein utilizing a member or element that can absorb forces/load applied by the bones that are joined by the joint may be desirable to treat afflictions such as osteoarthritis, trauma, or other pain-causing conditions in a joint. Preferably, the embodiments of the present invention are implanted subcutaneously and are extra-articular, peri-articular, or extra- or para-capsular of the treated anatomical joint.

Referring to FIGS. 1-2, forces occurring between members forming a body joint (anatomical joint) are described. The arrows 50 shown in FIG. 1 represent forces/load occurring between adjacent members 6, 7 of a body joint lacking an energy manipulation assembly 10 of the present invention. However, as shown in FIG. 2, in body anatomy incorporating the present invention, less forces/load are transferred to the bones and cartilage of the members defining the joint. Where the body joint is treated with the described energy manipulating is assemblies of the present invention, a portion of the forces/load between body members is absorbed by the energy manipulating assembly 10 (depicted as arrows 54 in FIG. 2). Accordingly, with the energy manipulating assembly 10 in place, less force is placed on the joint than when the assembly 10 is not present. The total load in FIG. 2 is shared between the force/load 56 carried by the joint and the force/load carried by the assembly 10.

The assembly 10 absorbs energy in the joint by application of a force in the direction of the arrows 54, which are generally in an axial direction of the joint in extension. The tension member of the assembly 10 applies a force in a direction substantially opposite to directions of load applied by the first and second members of the anatomical joint toward one another. This can also be described as applying a force in a direction of distraction, although actual distraction of the joint may or may not be present.

Although the assembly 10 is schematically represented as being installed on the medial side of the joint shown in FIG. 2, that the present invention is not limited to such an arrangement, as assembly 10 can alternatively be installed on the lateral side of the joint, or as pair of assemblies 10 can alternatively be installed, one on the medial side of the joint and one on the lateral side of the joint.

Figure 4:
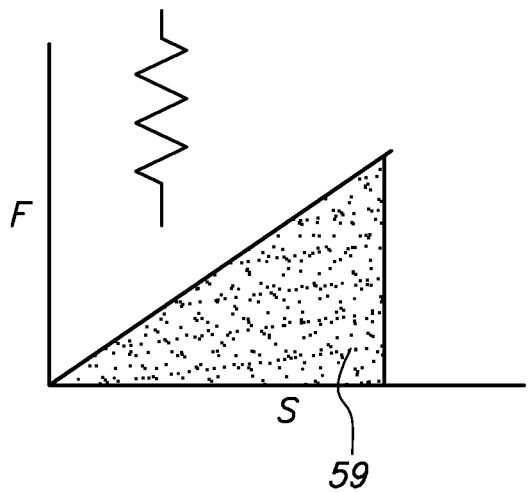
FIG. 4 is a graph of force versus displacement, illustrating the energy characteristics of a linear spring system.
Figure 5:
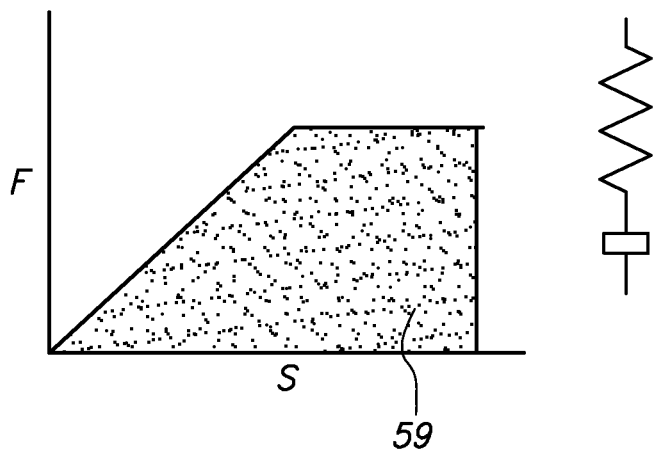
FIG. 5 is a graph of force versus displacement, illustrating the energy characteristics of a spring and dampening system.
Figure 6:
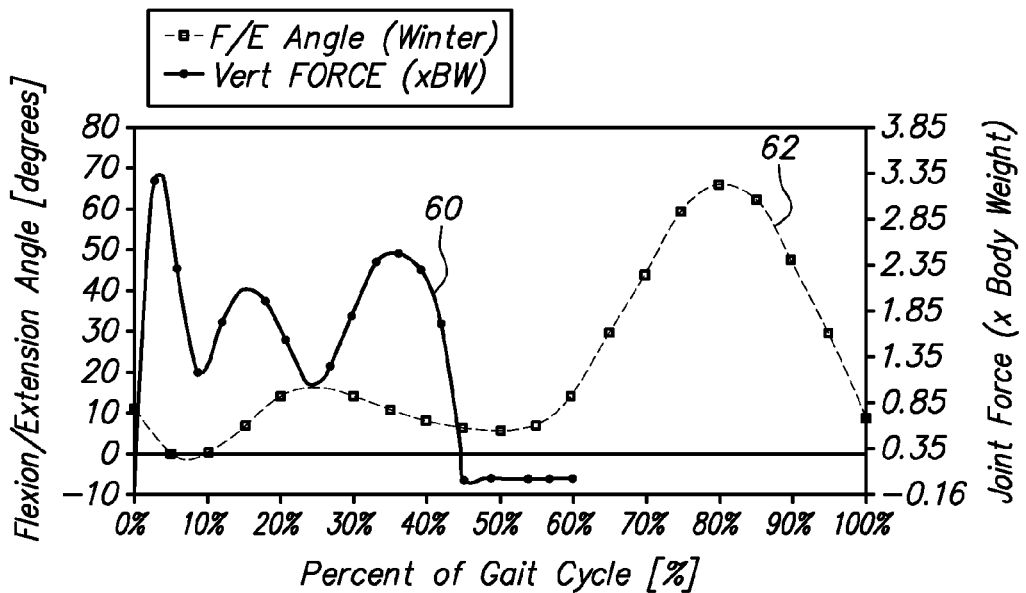
FIG. 6 is a graph, illustrating the flexion/extension angle and joint force existing in a gait cycle.

FIGS. 3-5 illustrate the relation between force (F) and displacement (S) between members of a body joint (where mass is constant). In a rigid body system (FIG. 3) which does not incorporate aspects of the present invention, there is no displacement and no energy absorption. In an energy manipulating system incorporating a single linear spring (FIG. 4), energy is absorbed in proportion to a spring constant (spring stiffness). The energy absorbed is represented by the shaded area 59 below the curve. As shown in FIG. 5, where a spring and dampener are used in combination, the energy absorbed 59 is a function of the spring constant and the dampener. It is these relationships which are considered in developing desired energy manipulating characteristics for an energy absorbing assembly for a joint.

Figure 7:
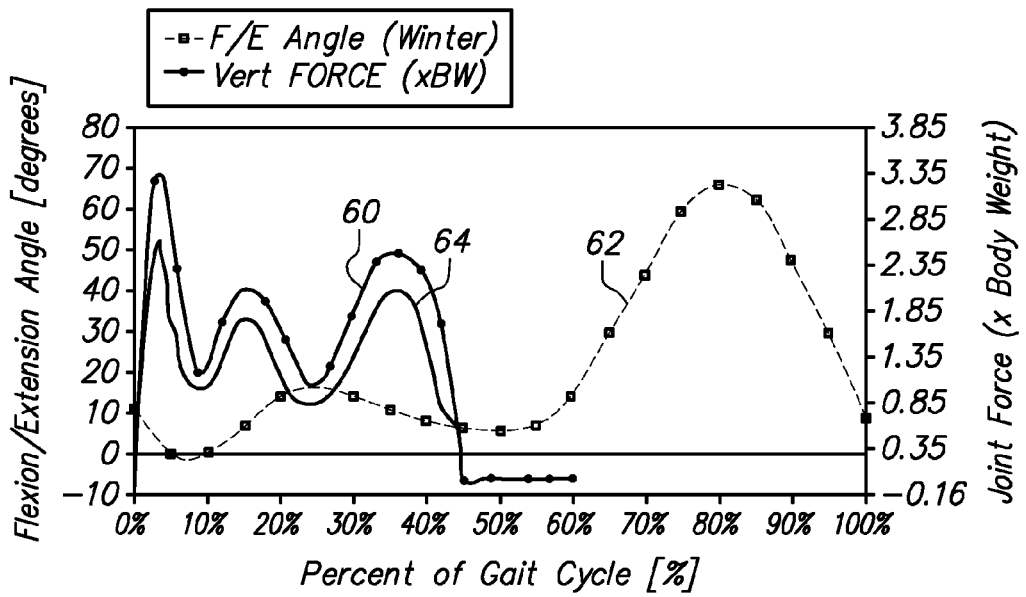
FIG. 7 is a graph, illustrating one approach to energy absorption on a gait cycle.
Figure 8:
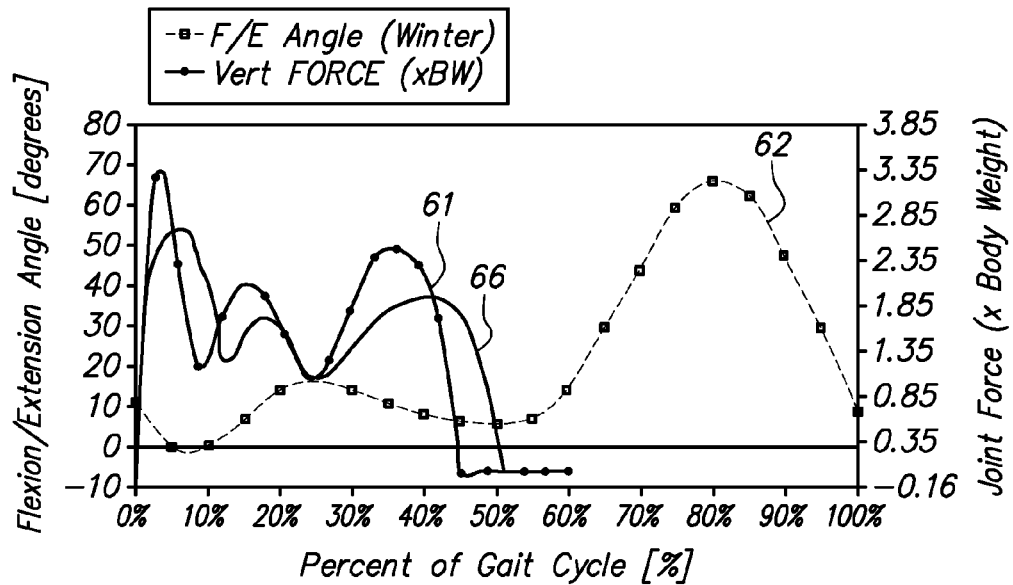
FIG. 8 is a graph, illustrating a second approach to energy absorption on a gait cycle.
Figure 9:
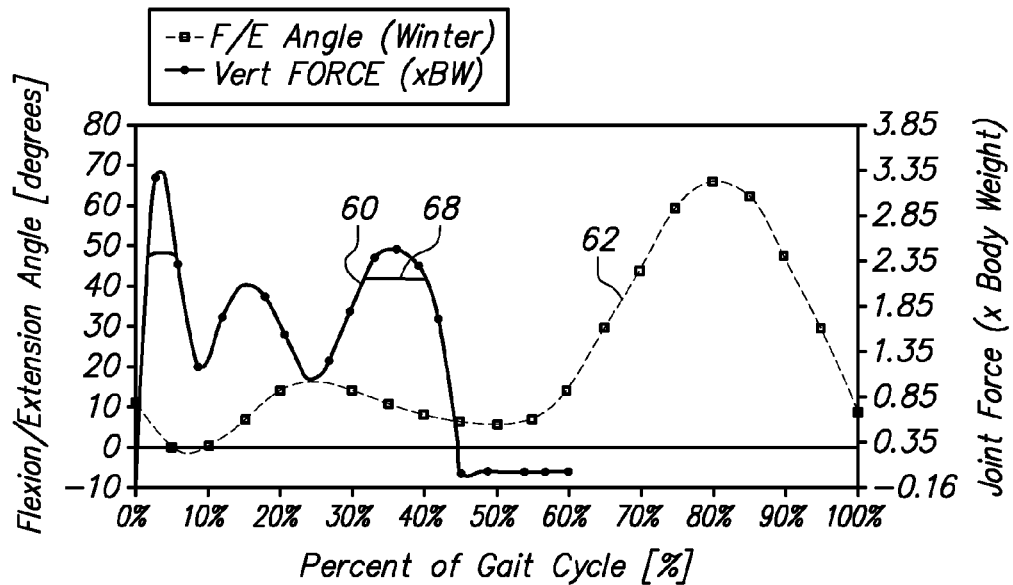
FIG. 9 is a graph, illustrating a third approach to energy absorption on a gait cycle.
Figure 10:
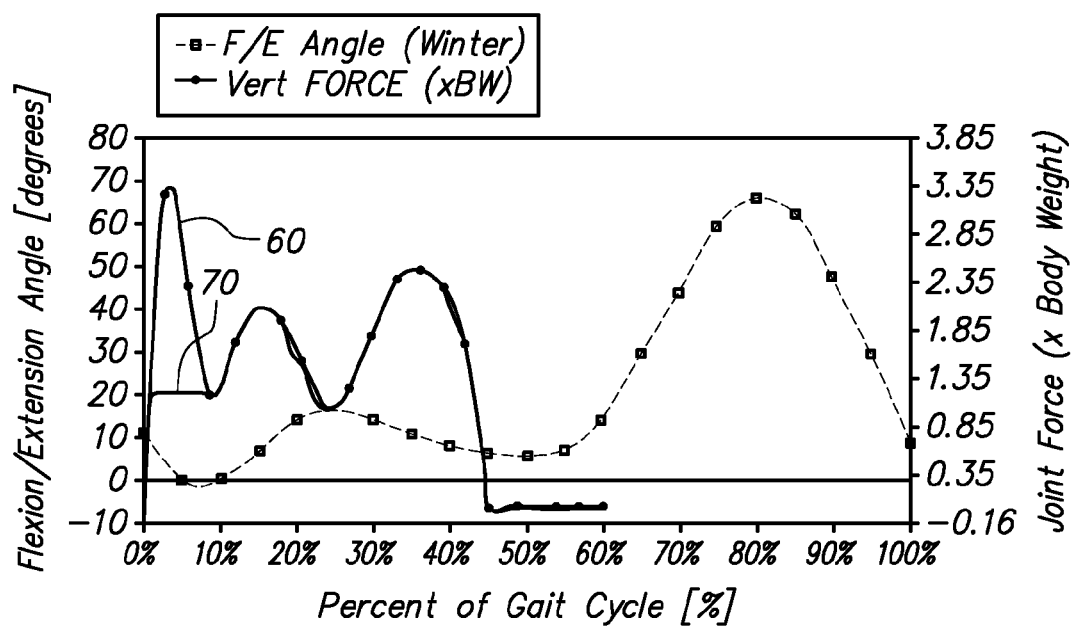
FIG. 10 is a graph, illustrating a fourth approach to energy absorption on a gait cycle.

Also considered are the forces existing through flexion and extension of an articulation cycle of the particular joint anatomy to be treated. Using the gait cycle of the legs of a human as an example, both the joint force and flexion/extension angle in degrees for a knee joint during walking can be plotted versus the percentage of the gait cycle completed with the gait cycle beginning at heel contact. A normal or expected relationship 60 of vertical forces generated through the gait cycle is depicted in each of FIGS. 6-10. Also depicted in FIGS. 6-10 is the flexion/extension angle 62 of the knee throughout the gait cycle. The expected relationship 60 of vertical forces during the gait cycle can be altered using certain of the embodiments of the energy manipulation assemblies of the present invention. As shown in FIG. 7, an energy manipulation assembly 10 according to the present invention can absorb energy by a substantially fixed proportion during a portion of the gait cycle. This is reflected by curve 64 in FIG. 7. Moreover, energy can be both absorbed and dampened as represented by curve 66 of FIG. 8 or alternatively, energy can be absorbed only above a fixed value as represented by curve 68 of FIG. 9. Additionally, as reflected by curve 70 of FIG. 10, energy can be absorbed in a fixed portion of the gait cycle or for a particular range of flexion/extension angle. It is to be recognized, however, that each of or one or more of these types of energy absorption can be combined in a desired system.

Figure 11:
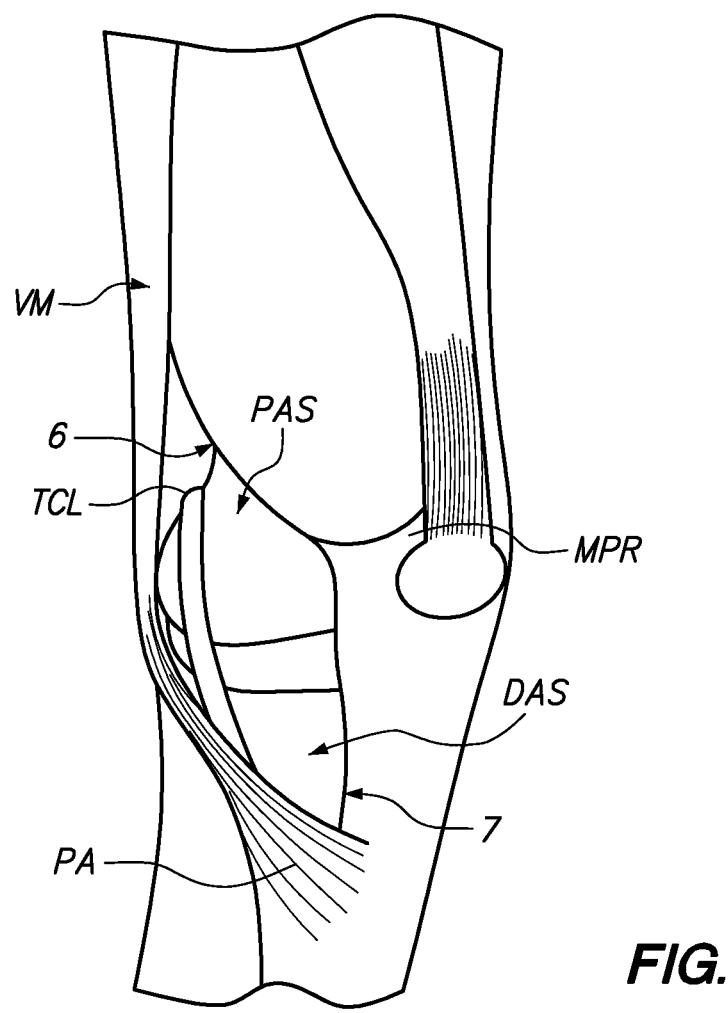
FIG. 11 is a perspective view, depicting anatomy of a typical knee joint.

Referring now to FIG. 11, the medial side anatomy of a typical knee joint is presented in a manner relating to an implantation procedure. Such a procedure could ultimately involve the implantation of devices such as those described below. Although the knee joint is being described here, it is contemplated these devices can also be placed at other articular synovial joints throughout the body and some non-articular, non-cartilaginous joints that are capable of motion in a flexion/extension direction that exceed forty-five degrees.

In a procedure seeking to transiently, variably reduce load or manipulate forces at a knee joint, a proximal attachment site (PAS) for it base of an energy manipulation device must be identified. Similarly, a distal attachment site (DAS) must also be selected. In a contemplated approach the medial proximal attachment site (PAS) can be located on a femur 6 in a space defined by the medial patellar retinaculum (MPR), the vastus medialis (VM) and the tibial collateral ligament (TCL). The distal attachment site (DAS) can be located on the tibia in a region defined by the medial patellar retinaculum (MPR) and the pes anserinus (PA).

Figure 12A:
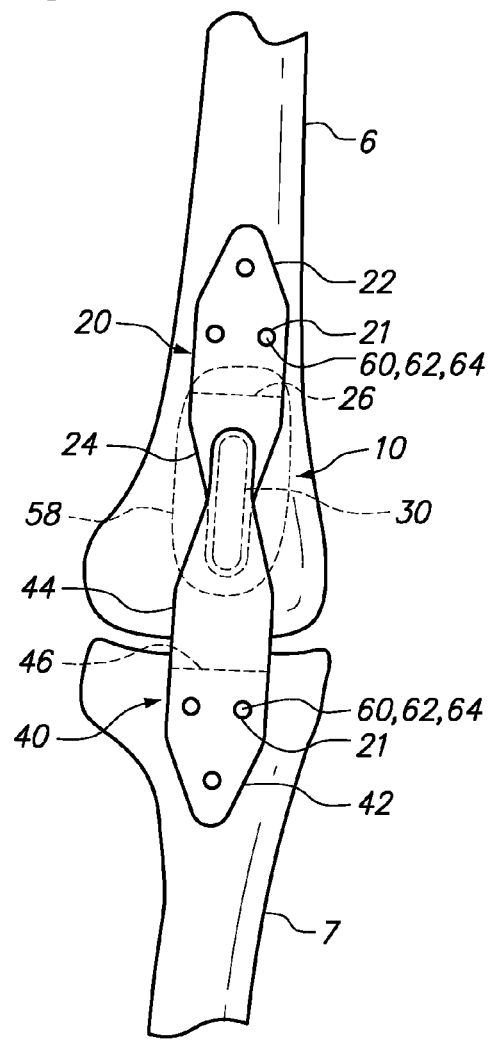
FIG. 12A is a medial side view of one embodiment of an assembly installed on a left knee joint according to the present invention.
Figure 12B:
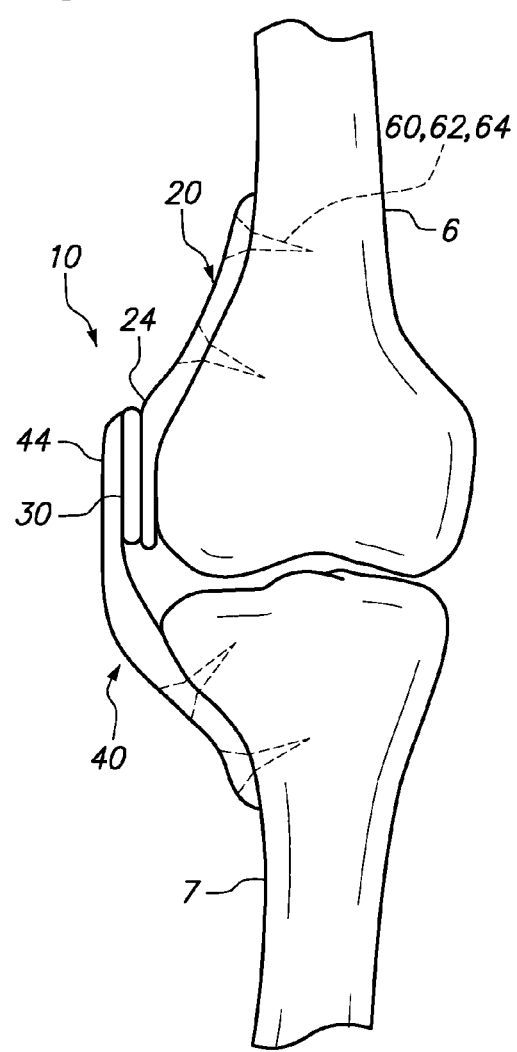
FIG. 12B is an anterior view of the left knee joint and assembly shown in FIG. 12A.

FIGS. 12A-12B show a medial side view and an anterior view of one embodiment of an assembly or device 10 according to the present invention installed medially on a knee joint. Assembly/device 10 includes a first component 20 (in this example, first component 20 is a femoral component) and a second component 40 (in this example, second component 40 is a tibial component). The femoral component 20 is configured to be attached to a distal end portion of a patient's femur 6. The femoral or first component 20 includes a first base 22 that is configured to be anchored to a first bone that connects at the joint, and the tibial or second component 40 includes a second base 42 that is configured to be anchored to a second bone that connects at the joint.

First component 20 includes a first extension member 24 that may be integral with first base member 22 or may be removably fixed thereto at 26, such as by a dovetail connection with or without a locking screw, or other mechanical connection that can be locked during use, but unlocked at any such time as separation of the components 22, 24 is desired. A removably fixed extension member may be preferable for some implantation methods, particularly some minimally invasive methods, although not necessarily required. Likewise, second component 40 includes a second extension member 44 that may be integral with second base member 42 or removably fixed thereto at 46.

The opposite ends of extension members 24 and 44 that are not fixed to base members 22 and 42 are interconnected by tension member 30, such that free end portions of extension members 24, 44 are joined by tension member 30. Note that when assembly/device 10 is installed on the bones joined by as joint to be treated by the assembly/device 10, the extension members 24, 44 overlap when the anatomical joint is in the full extension orientation shown in FIGS. 12A and 12B. Due to this overlap, forces applied against the joint by the bones 6, 7 drive the end portions of the extension members 24, 44 connected by tension member 30 further away from one another. This causes deformation/lengthening of tension member 30, which results in energy manipulation/absorption by the tension member of a portion of the energy resulting from the applied forces. The partial transfer of load to the tension member 30 reduces the amount of force applied to the anatomical joint surfaces.

Tension member 30 may comprise, for example, one or more extension springs, one or more elastomer bands, a combination of one or more springs and one or more elastomer bands, or a combination of an of the foregoing with a dampening member such as a viseoelastic band, or other members that resist extension, such as another extension spring, an elastic band, or a dampening system that resists rapid extension. In the example shown in FIGS. 12A-12C, tension member 30 is an elastomeric band that loops around pins 32 extending from extension members 24, 44 at the free end portions thereof. Pins 32 extend transversely from the surface of the extension members 24, 44, transverse to the longitudinal axes of the respective extension members 24, 44. In this arrangement, pins 32 and tension member 30 form two pivoting joints 33, one at the location where tension member 30 connects with the pin 32 on extension member 24 and one where the tension member 30 connects with the pin 32 on the extension member 44. Alternative rotatable and non-rotatable connections can be made when connecting tension member 30 to extension members 24, 44.

Figure 12C:
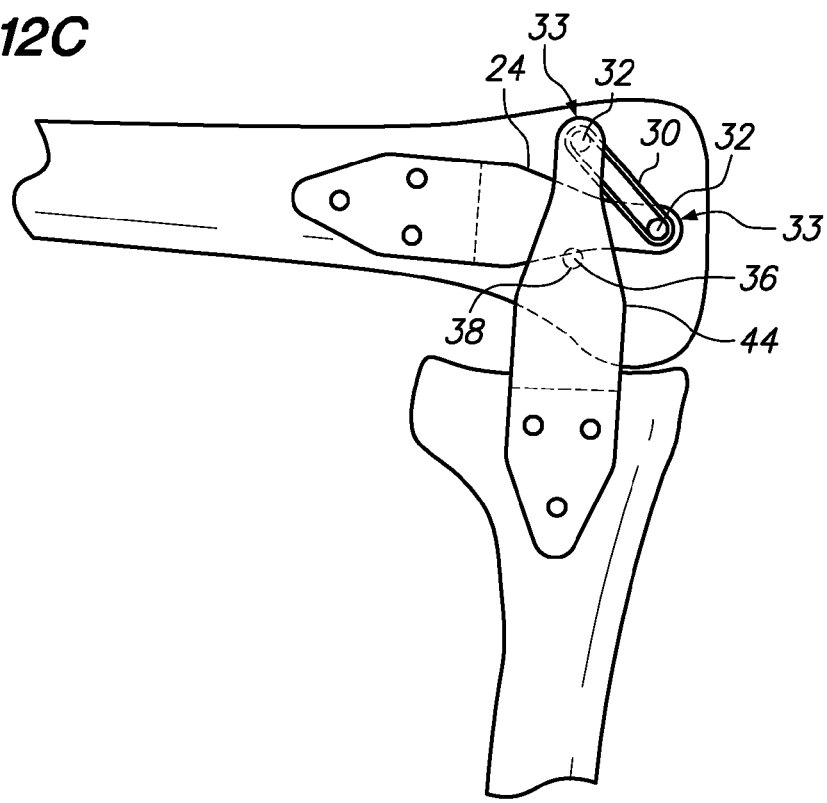
FIG. 12C shows the knee joint and assembly of FIG. 12A when the knee joint is in flexion.
Figure 12D:
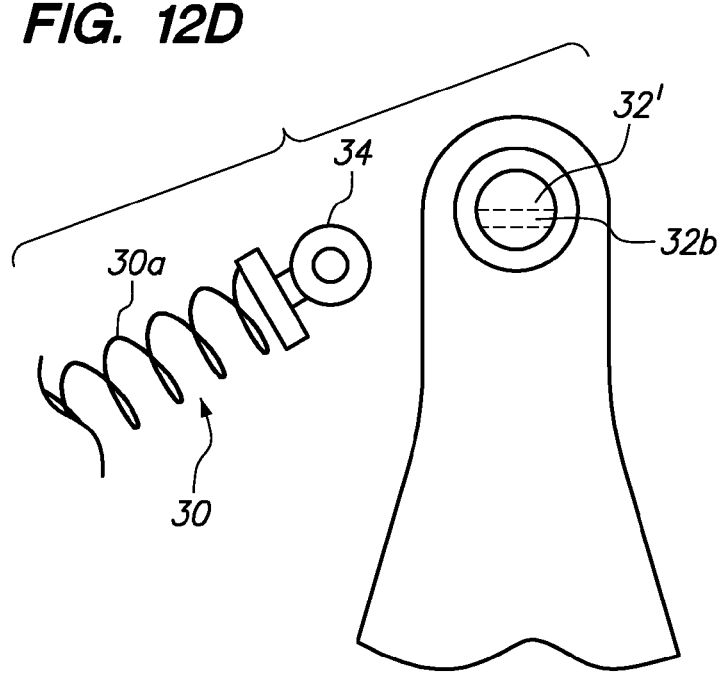
FIG. 12D illustrates an alternative connection mechanism for connecting a tension member to an extension member according to the present invention.

In one non-limiting alternative embodiment, the extension members are provided with rotational joints 32', an example of which is illustrated in FIG. 12D. Tension member 30 (including spring 30a) can then be fixed to the portion of rotating joint 32' that is rotatable relative to the extension member 24, 44 by mechanical fixation. Such mechanical fixation being performed by screwing, bolting, riveting, passing an end of tension member 30 through an optional opening or bore 32b and attaching an anchor to the end or otherwise enlarging the end so that it cannot pass back through the opening 32b and/or adhering. FIG. 12D also illustrates a partial view of an embodiment of tension member comprising an extension spring 30a, having ends 34 with rings or eyelets configured to be screwed, pinned or otherwise fastened to rotational joints 32'. Note that rings or eyelets/ends 34 are also rotatable about the longitudinal axis of the spring 30, which allows relative rotation between extension members 24, 44, about the longitudinal axes of the bones to which extension members 24, 44 are attached, during movement of the assembly 10 from extension to flexion and back. Of course, elastomer bands used in tension member 30 also allow such relative rotation.

In at least one embodiment, one or more bones forming the anatomical joint which the assembly/device 10 is to be installed to are three-dimensionally scanned. From the scans of the one or more bones, one or more components of the assembly/device 10 can be custom designed to follow the contours of the one or more bones to which the component(s) is/are to be installed. Alternatively, the components 22, 24, 42, 44 can be provided in one or more standard sizes designed to fit most anatomical geometries. Whether or not the assembly/device is custom designed, if the components (e.g., 24 and 44 and, optionally, 22 and 42) are for temporary implantation, they may be molded components, molded from suitable polymers including polyethylene. Alternatively, for longer term use, the components (e.g., 22, 24, 42 and 44) may be machined or otherwise formed from titanium, chromium cobalt alloys, stainless steel, ceramic or other biocompatible materials suitable for making implantable devices.

The components 20 and 40 are secured to the bones by one or more fasteners, such as screws, including locking screws 60, bicortical screws 62, compression screws 64, or the like, passed through openings 21 and screwed into the bones, (e.g., the femur 6 and tibia 7, respectively, as shown in FIG. 12B). Alternative fasteners include, but are not limited to dynamic lag screws.

During loading of the anatomical joint (such as the knee during walking), the forces applied through assembly/device 10 cause tension member 30 to deform when the joint is in extension. Thus, the device 10 is designed to be implanted in a configuration such that the tension member is at least partly stretched when the joint is placed in extension. For a knee joint the portion of the gait cycle in which the knee is in extension is the time of highest loading of the joint and the greatest need for shifting of load to the energy absorbing device. This results in tension member 30 taking up (absorbing) the distance change between components 24, 44 under loading of the natural joint. This deformation absorbs some of the energy of the forces/load, thereby reducing the amount of force/load that is applied through the natural joint, as was described above. Additionally, tension member 30 can deform (e.g., twist) to accommodate relative axial rotation between members 20, 40 in addition to, or alternative to any rotational joints provided in tension member 30, such as described above.

During flexion of the anatomical/natural joint, the forces are also at least partially removed from tension member 30, whereby tension member contracts axially back to its non-extended state. As described above in reference to FIG. 6, the flexion portion of the gait cycle for a human knee joint is the portion of the gait cycle experiences the lowest loads or joint forces. Thus, there is little need for the tensioning member 30 to provide a biasing force at flexion angles beyond about 30-45 degrees. Accordingly, in the example of a knee joint, the positioning of the components 20, 40 and the tightness or nominal length of the tension member are preferably arranged for complete unloading of the tension member 30 when the knee of the patient is between about 30 and 90 degrees of flexion. The desirability of complete unloading of the tension member 30 at high flexion angles is also desired to prevent application of a distraction force to the joint in an unloaded and seated position which can tend to overstretch the joint ligaments. Although the desired maximum tension of the tensioning member 30 at full knee extension and minimum tensioning of the tension member 30 at full flexion has been described for the knee joint, it would be understood that for other joints the maximum and minimum tensioning could be determined upon analysis of the cyclic loading of the particular joint.

The amount of force or load provided by the tension member 30 will vary depending on the joint for which the assembly 10 is used. In addition, the amount of force provided by the tension member can vary depending on the patient size, the treatment plan, injury or disease condition, or progression of disease. For treatment of osteoarthritis in a knee the tension member can be designed to provide for about 4 mm of travel between the tensioned and untensioned states and a pre-determined load of 10-60 pounds, preferably about 30-50 pounds to cause the tension member to stretch.

Note that in FIGS. 12A-14B, the terminal end portions of the femur 6 and tibia 7 are depicted without surrounding tissue, for purposes of simplicity and clarity. It is noted that the bases 22 and 42 are contoured to match potential mounting surfaces of the lemur and tibia. The size and shape of these components may vary depending on the joint to which the energy absorbing assembly is affixed.

Since the assembly 10, is positioned subcutaneously and travels alongside the muscles and ligaments of the joint, optionally, assembly can be provided with a subcutaneous tissue barrier in the form of a sheath 18 (e.g., see phantom lines in FIG. 12A), preferably expanded polytetrafluoroethylene (ePTFE), which encloses various parts of the system and excludes surrounding tissue. It is contemplated that the subcutaneous tissue barrier can be formed from or coated alternatively with a tissue in-growth substance or for that matter, substances which inhibit such in-growth. For example, it may be desirable that one or more sides or portions of the assembly 10 enclosed by the sheath 58 be affixed to surrounding tissue whereas it may be advantageous that other portions of the system be free to move with respect to surrounding tissue. Of course, tension member 30, and extension members 24, 44 remain free to move relative to the sheath 58.

FIG. 12C illustrates an orientation of assembly/device 10 when the joint (in this case, the knee joint) is in flexion. When the anatomical joint moves from extension (e.g., FIG. 12A) toward flexion (e.g., FIG. 12C), the bending of the anatomical joint causes extension members 24, 44 to rotate relative to one another in a scissoring action. Conversely, when the anatomical joint moves from flexion toward extension, the scissoring action of the extension members 24, 44 moves them back toward their aligned, overlapping configuration shown in FIG. 12A. Preferably, point locations 36 on the extension members 24, 44 about which the extension members rotate, relative to one another, during the scissoring action are intermediate of the locations where tension member 30 connects to extension members 24, 44. Preferably this location about which the tension members 24, 44 rotate is about midway between the locations where tension member 30 connects to extension members 24, 44, as this minimizes the amount of extension by either extension member 24, 44 past the other during rotations from extension to flexion back to extension. Further, the pivot point locations 36 on extension members 24, 44 substantially maintain alignment over the full range of motion of the anatomical joint, as the extension members 24, 44 rotate from extension through flexion and back to extension. Further, upon implantation of assembly/device 10, assembly/device 10 may be anchored in a position such that the pivot point locations 36 are substantially aligned over a bone forming a part of the anatomical joint in a location that approximates the axis of rotation of that bone during movements of the anatomical joint through the range of motion. For example, for a knee joint the pivot point locations are substantially aligned over the axis of rotation of the knee.

It has been found by the inventors that locating the pivot point locations 36 substantially aligned over the midpoint of Blumensaat's line in a true lateral view or within plus or minus five millimeters of the midpoint of Blumensaat's line results in preferable assembly/device 10 function. One method for locating a location over which the pivot points 36 are to be located, is to use imaging equipment to form an image of the knee or other joint being treated, such as by using fluoroscopy and/or three-dimensional navigational software such as that available from Stryker, Medtronic or Brainlab. The members defining the joint are placed in a full lateral position and perpendicularly to the receiver of the imaging device. The proximal joint member is then fixed using a vacuum splint/sandbag or similarly effective device. As one example for implantation to treat the knee joint, the Blumensaat's line of the femur bone 6 can be used as a landmark for locating the various components of the device/assembly 10 so that pivot points 36 are located above a location that is at or near the midpoint of the Blumensaat's line. Blumensaat's line is a line formed by the roof of the intercondylar notch between the two femoral condyles. The midpoint of the Blumensaat's line has been determined to quite accurately approximate the center of rotation for a knee joint.

Alternatively, it is further contemplated that other regions can represent possible locations of a femoral rotation point on the medial chondyle. In order to select such an alternative point, the surface area of the medial chondyle is mapped to determine regions corresponding to changes in device 10 length of a potentially implanted energy manipulation assembly/device 10 while the joint is moved from full extension to full flexion. Areas of device 10 increasing length and decreasing length can be mapped. Moreover, areas can be identified where there is an initial device 10 length increase then followed by a length decrease, and where there is an initial length decrease followed by increasing length. Mapping of areas of overlap between these various areas represent transitions from one region to a next. An area representing in minimal displacement can also be identified. This information is then employed to identify the various points of rotation best suited for a particular energy manipulation assembly implant 10. The fixation of both bases 22 and 42 are determined by the location of placement of the pivot point locations 36 over the identified area representing minimal displacement.

Furthermore, an approach to proper implant placement can involve observing changes in device length (i.e., wherein "device length" in this instance is defined by the distance between the fixation points of the tension member 30) at 90° flexion relative to a fully extended length. These length changes are measured relative to a femoral rotation point at a midpoint of the Blumensaat's line (in the case of a knee joint). The device and rotation point is then selected based upon desired measurement changes. The fixation locations for base 22 on the femur and base 42 on the tibia are then determined by placing the pivot point locations 36 over the selected rotation point while the femur 6 and tibia 7 are in full extension, and aligning the bases 22, 42 with the longitudinal axes of the bones 6, 7 respectively. Optionally, a through hole 38 may be provided in each of extension members 24, 44 with the pivot point locations 36 serving as the centers of the through holes. In this case, a Kirschner wire (K-wire) can be inserted into the location having been identified to displace minimally over the range of motion of the anatomical joint, and then the extension members can be slid over the K-wire, allowing the K-wire to pass through the holes 38, thereby aligning the pivot point locations 36 with the identified area of minimal displacement.

Likewise, holes 38 can be employed tot the other noted methods of locating where, on the bone, the pivots points are to be positioned. For example, a K-wire can be inserted into the femur at about a midpoint along the Blumensaat's line. Preferably, the K-wire is inserted about 0.5-2 mm above and anterior of the midpoint of Blumensaat's line.

By maintaining the pivot points 36 over this estimated rotation point (area of minimal displacement) and temporarily fixing bases 22 and 42 at the fixation locations on the femur 6 and tibia 7 dictated by the placement of the pivot point locations 36, while the knee joint is in full extension, the knee joint can then be manipulated through its range of motion to simulate the gait cycle and observe the elongation of the assembly 10. The assembly 10 should typically be at its most compressed when the knee joint is in full extension (and thus tension member 30 is at its most elongated) and then should gradually elongate over at least a portion of the gait cycle toward full flexion, while tension member 30 at the same time gradually shortens. In other words, the tension member 30 is in its longest configuration and providing the most tension when the knee is in full extension and the tension member 30 provides less tension or preferably no tension when the knee is in full flexion. The best rotation point can be determined empirically by moving the location of K-wire insertion in the femur 6 until the actions of the assembly over the course of the gait cycle have been optimized.

In an alternative approach, a circle guide can be placed over the natural joint with the center thereof configured at a midpoint of the Blumensaat's line, as described in U.S. Patent Publication No. 2008/0275561 and titled Extra-Articular Implantable Mechanical Energy Absorbing Systems and Implantation Method, which is incorporated herein by reference in its entirety. It has been found that when considering device elongation and compression, along with anterior and posterior device positioning as well as flexion degrees during a patient's gait, that +/−5 mm, and preferably +/−3 mm, from a center point of a Blumensaat's line can be a starting reference point. At this point, the circle guide can be used to confirm that the tibial plateau at 90° flexion is 1-2 rings on the circle guide outside of an initial matching circle at 0° flexion, if the assembly 10 selected for the patient is only meant to extend during flexion. At a mid-point of the Blumensaat's line and perpendicularly thereto, the physician will then insert a rigid guide or K-wire through a center guide hole of the circle guide that has been previously locked in place. The K-wire includes a sharp terminal tip for entering bone and thus the K-wire can either be drilled into the bone or tapped in by farce. After the K-wire has been fixed perpendicularly to the bone, the circle guide is removed and the K-wire is shortened leaving approximately one inch of wire protruding through the skin. Assembly/device 10 may then be placed over the K-wire, such as by sliding through holes 38 over the K-wire and the locations of fixation of bases 22, 42 and the device sizes if available can be estimated in the manner described above, while using remote image techniques.

Once the rotation point (location of pivoting points 36) has been located and fixation locations of the bases 22, 42 have been estimated, assembly/device 10 can be removed off of K-wire and a femoral incision can be made superior to the K-wire. Additionally, a tibial incision can be made interior to the K-wire. Fascia and tissue are then manipulated to expose bone periostium in the region of anticipated base attachments to the femur 6 and tibia 7. A subcutaneous channel is then formed either by hand or with blunt instrumentation to connect the two incisions. Alternatively, only one incision can be used from which to form a subcutaneous channel of equal length to the one described above that connects the pair of incisions. Further alternatively, one long incision can be formed with a length of the previously described subcutaneous channel. Further alternatively, a single small incision can be made at the center (e.g., location of the K-wire) and a tunnel can be formed to extend superiorly and inferiorly therefrom. In any case, assembly/device 10 is inserted either into the elongated incision, or through the subcutaneous tunnel to place the pivot points 36 over the rotation point having been previously determined. In instances where the K-wire is present through holes 38, the assembly 10 may be slide over the K-wire as noted above.

The bases 22, 42 can next be fixed to the femur 6 and tibia 7 at the previous located fixation locations, the fascia, tissue and periosteum having been already previously manipulated to expose the fixation locations on the bone. The bases 22 and 42 are affixed to the femur 6 and tibia 7, respectively, using bone screws as noted above, and this may be accomplished under fluoroscopic visualization, for example. Prior to completely turning the screws to fix the bases 22, 42, further adjustment may be performed. Once the screws 62, 62, 64 have been fully torqued down to fix the positions of bases 22, 42, the K-wire, if present, can be removed from through holes 38 and from the patient. It is to be further recognized that various angles of insertion of the bone screws can be used to aid in providing attachment support in a multitude of directions. Moreover, bi-cortical penetration of the bone screws is contemplated for certain applications.

In one approach, it is contemplated that bicortical screws can be polyaxial because their trajectory will be fixed by the bicortical purchase. Their trajectories can either diverge or converge by about 15 to 30 degrees to improve pull out strength but the exact angle is not critical, so the technique can be simplified by letting them rotate in a small cone. Further, the unicortical screws can have fixed trajectories. This will increase their stability that they may lack because of the unicortical purchase. The trajectories should either converge or diverge as above but the angles will be set. It may further be desirable to use a resorbable bone void filler under the bases to eliminate gaps and prevent ingrowth of fibrous tissues. An anti back-out feature is contemplated for the screws in certain applications. Examples of anti back-out features include locking screws which heads threaded into the bases or rotating locking mechanisms on the bases which partially cover the screw heads.

Further details of methods described above, as well as alternative techniques and methods for locating, orienting, positioning and implanting assembly/device 10 can be found in U.S. Patent Publication No. 2009/0014016 titled Surgical Implantation Method and Devices for an Extra-Articular Mechanical Energy Absorbing Apparatus, which is hereby incorporated herein, in its entirety, by reference thereto.

Figure 13A:
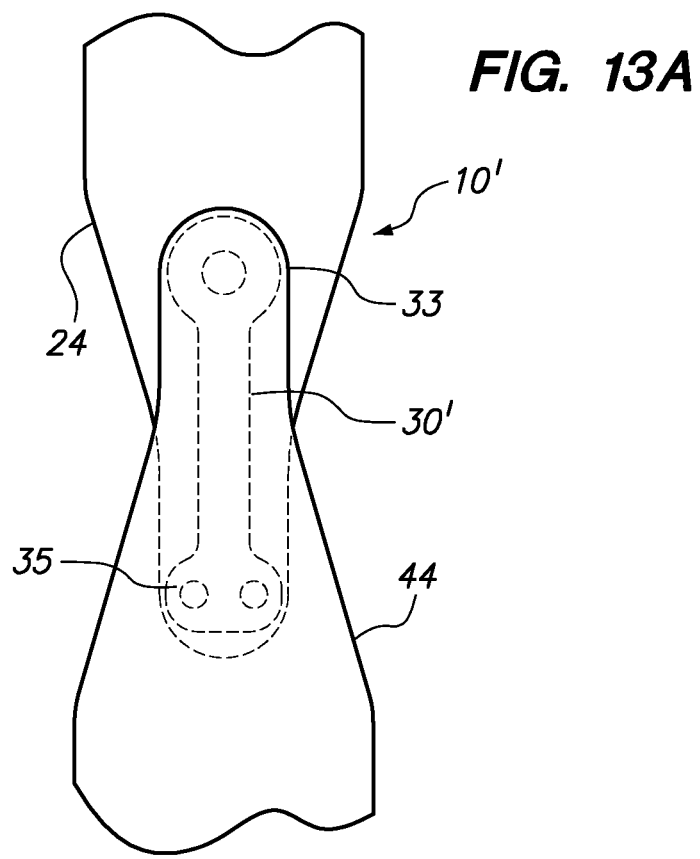
FIG. 13A is a partial view of another embodiment of an assembly according to the present invention.
Figure 13B:
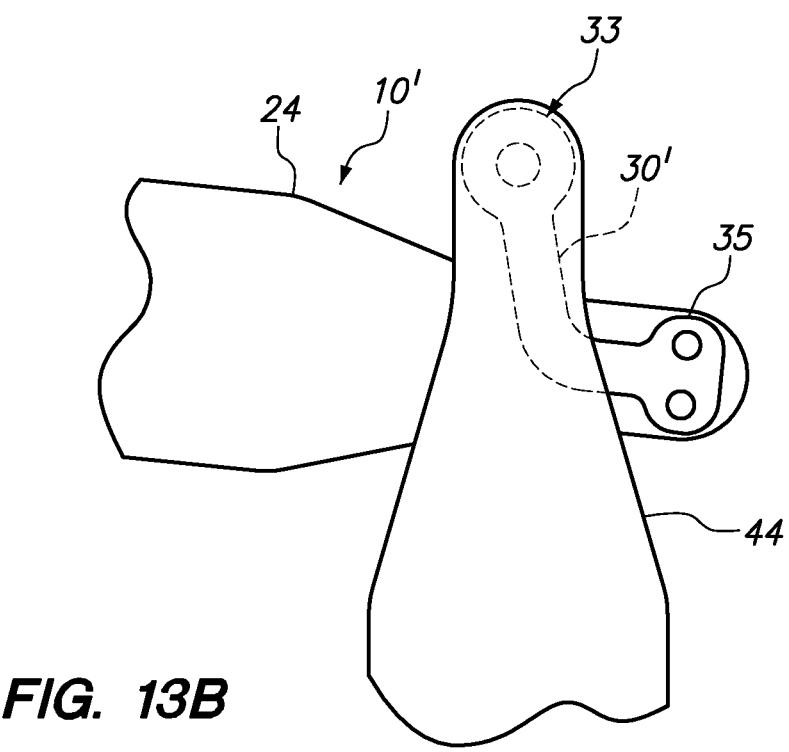
FIG. 13B shows the partial view of FIG. 13A, but in an orientation assumed when the assembly is installed on a joint in flexion.

FIGS. 13A-13B illustrate another embodiment of an assembly/device 10' according to the present invention. FIGS. 13A-13B show a partial view of assembly device 10 as it would appear on a side view of a knee joint when installed thereon, with FIG. 13A showing the orientation of assembly/device 10' when the anatomical joint is in extension and FIG. 13B showing the orientation of assembly/device 10' when the anatomical joint is in flexion. As installation/implantation of device/assembly 10' is performed in essentially the same manner as installation/assembly of device/assembly 10, and bases 22, 42 are essentially the same in assembly/device 10' as in assembly/device 10, neither bases 22, 42, no the anatomical joint are illustrated in FIGS. 13A-13B for simplicity and so as to focus on the differences in the embodiment of FIGS. 13A-13B relative to the embodiment of FIGS. 12A-12D.

Tension member 30' is connected to extension members 24 and 44 via only one pivoting or rotational joint 33 connecting to one of the extension members 24, 44 at one end of the tension member 30', while the opposite end of the tension member 30' is fixed to the other of the extension members 24, 44 and is not rotatable with respect thereto. For example, the end of tension member 30' may be fixed to the narrower end portion of either extension member 24 or extension member 44 by screwing, bolting, stapling, riveting and/or adhering the end portion of tension member 30' thereto, so that relative rotation of these fixed parts is not permitted. Note that although extension member 44 is shown in FIG. 13A as connected to tension member 30' by a pivoting or rotational joint, while tension member 30' is shown fixed relative to extension member 24 and thus prevented from rotating with respect thereto, that an opposite arrangement could be substituted, wherein extension member 24 is rotationally connected to tension member 30' and extension member 44 is connected to tension member 30' with a fixed joint that prevents rotation.

In either case, the flexibility of tension member 30' allows it to bend near the end where it is fixedly attached and prevented from rotating, while at the same time, the rotationally connected end of tension member 30 rotates relative to the extension member so that no or much less bending occurs near this end of the tension member 30' during flexion of the anatomical joint, as illustrated in FIG. 13B. Additionally, the tension member 30' also extends/deforms longitudinally to absorb energy in like manner to that described above with regard to the embodiment of FIGS. 12A-12D.

The tension members 10, 10a, 10' in any of the embodiments described herein can be either permanently or removably affixed to the extension members 24, 44. When the tension members 10, 10a, 10' are permanently fixed to the extension members 24, 44 the entire device/assembly 10 can be implanted as a single piece. In this case it may be desirable to include a removable retention sheath or other fixation mechanism to maintain the assembly in a preferred configuration, i.e. with the tension member is tension during assembly. Such a removable sheath could be removed after fixation of the two bases 22, 42 to allow functioning of the device. Alternatively, when using removable tension members 10, 10a, 10' the tension members can be attached to the extension members 24, 44 either before or after fixation of the bases 22, 42 to the bones. In the event that the tension members are attached after fixation of the bases, a tensioning device may be provided to extend the tension members during attachment. Alternately, the tension members can be attached in an untentioned configuration if the joint is placed in a position, such as full flexion, where the tension member is designed to be untensioned.

In one further embodiment, the tension member 10, 10a, 10' can be provided connected to the extension members 24, 44. In this case, one or more of the extension members 24, 44 can be connected to the associated bases 22, 42 after these bases are fixed to the bone. The connection of the extension members 24, 44 to the bases 22, 42 at the line 46 shown in FIG. 12a can be via a quick connect coupling, such as a coupling including a tapered bore and corresponding tapered post.

Figure 14A:
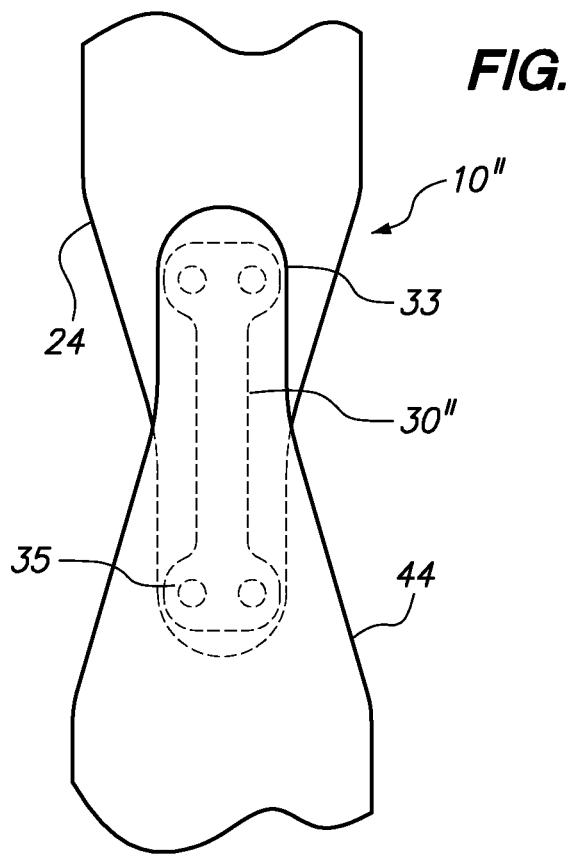
FIG. 14A is a partial view of another embodiment of an assembly according to the present invention.
Figure 14B:
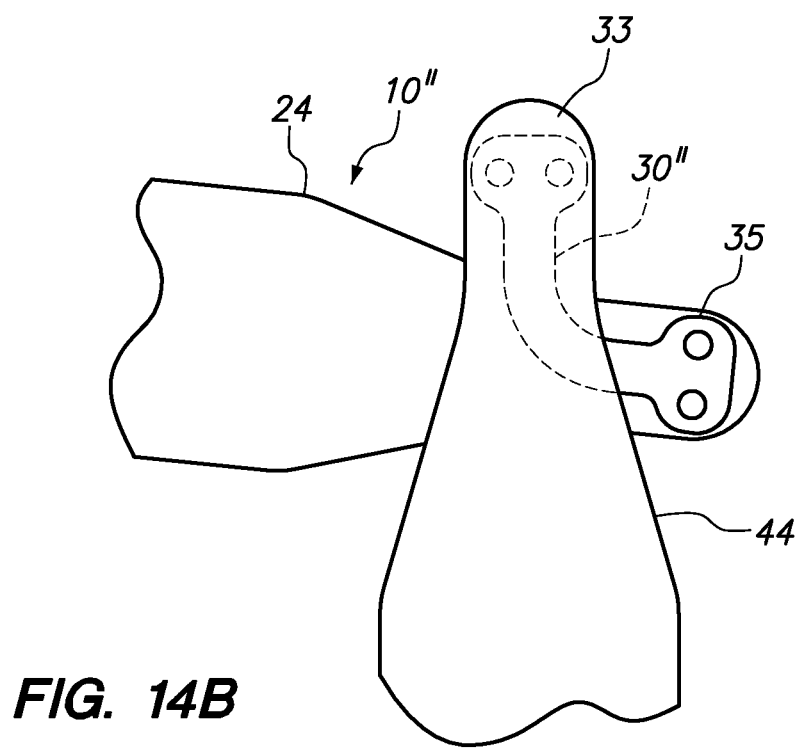
FIG. 14B shows the partial view of FIG. 14A, but in an orientation assumed when the assembly is installed on a joint in flexion.

FIGS. 14A-14B illustrate another embodiment of an assembly/device 10" according to the present invention. FIGS. 14A-14B show a partial view of assembly device 10" as it would appear on a side view of to knee joint when installed thereon, with FIG. 14A showing the orientation of assembly/device 10" when the anatomical joint is in extension and FIG. 14B showing the orientation of assembly/device 10" when the anatomical joint is in flexion. As installation/implantation of device/assembly 10" is performed in essentially the same manner as installation/assembly of device/assembly 10 and 10', and bases 22, 42 are essentially the same in assembly/device 10" as in assembly/device 10 and 10', neither bases 22, 42, nor the anatomical joint are illustrated in FIGS. 14A-14B for simplicity and so as to focus on the differences in the embodiment of FIGS. 14A-14B relative to the embodiment of FIGS. 12A-12D and the embodiment of FIGS. 13A-13B.

Tension member 30" is connected to extension members 24 and 44 via fixed connections, such that neither end of tension member 30" is rotatable relative to the respective extension member 24, 44, that it is fixed to. For example, the ends of tension member 30" may be fixed at 33 and 35 to the narrower end portion of extension members 44 and 24, respectively by screwing, bolting, stapling, riveting and/or adhering the end portions of tension member 30" thereto, so that relative rotation of these fixed parts is not permitted.

The flexibility of tension member 30" allows it to bend between the ends where it is fixedly attached and prevented from rotating, as illustrated in FIG. 14B. Additionally, the tension member 30' also extends/deforms longitudinally to absorb energy in like manner to that described above with regard to the embodiments of FIGS. 12A-13B.

Figure 15B:
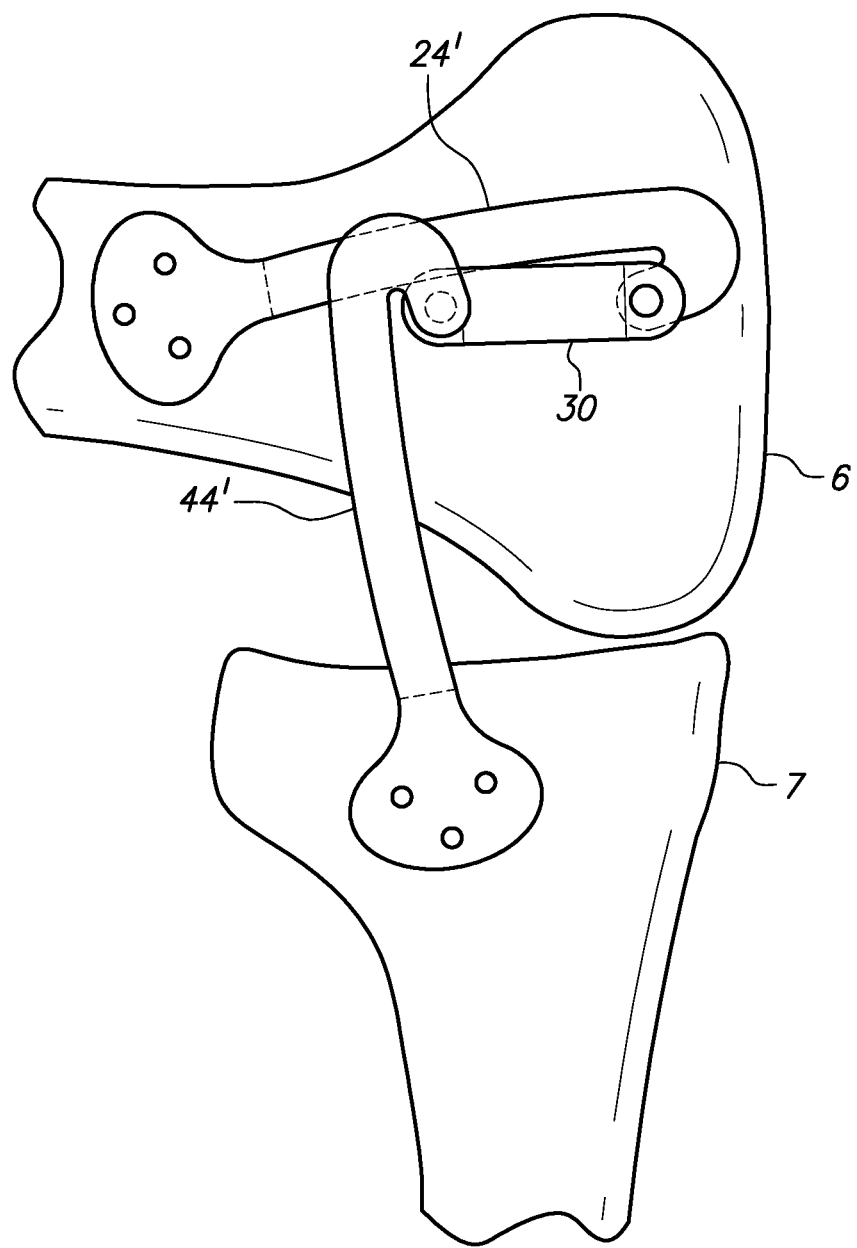
FIG. 15B is a view of the assembly and knee joint of FIG. 15A, when the knee joint is in flexion.

FIGS. 15A-15B illustrate another embodiment of an assembly/device 10'" according to the present invention. FIGS. 15A-15B show a view of assembly/device 10" as installed on a medial side of a knee joint, when in extension (FIG. 15A) and in flexion (FIG. 15B). In this embodiment, extension members 24' and 44' are shaped/curved so that they do not overlap one another when installed on an anatomical joint and when the anatomical joint is in extension, as illustrated in FIG. 15A. In the embodiment shown, extension members 24', 44' are substantially J-shaped, although other curved shapes may be substituted, as long as they function to prevent overlapping of the extension members as described. Preferably, extension members 24', 44' also do not overlap when the anatomical joint is in extension (e.g., see FIG. 15B) or during any orientation of the anatomical joint over the entire range of motion. Because the extension members 24', 44' do not overlap with one another, this embodiment can be made to have to significantly lower profile than earlier described embodiments, which can be advantageous at least for cosmetic reasons.

Tension member 30 functions in the same manner as described in previous embodiments above. As shown, tension member 30 is connected via a pivot point at both connection locations. Alternatively, tension member 30' may be connected to extension members 24' and 44' via only one pivoting or rotational joint connecting to one of the extension members 24', 44' at one end of the tension member 30', while the opposite end of the tension member 30' is fixed to the other of the extension members 24', 44' so as not to be rotatable with respect thereto.

The bone contacting surfaces of any of the bases 22, 42 described herein can be modified to induce bone growth. Ostenintegration can be obtained through mechanical interlocking or as a result of chemical loading. For example, the bone contacting surfaces may be coated with bone morphogenic protein 2 (BMP-2), hydroxyapatite (HA), titanium, cobalt chrome beads, or any other osteo-generating substance. According to one embodiment, a titanium plasma spray having a thickness of approximately 0.033 in.±0.005 in. is applied to the inner surface 28. In another embodiment, a HA plasma spray having a thickness of approximately 35 μm±10 μm is applied alone or in combination with the titanium plasma spray coating to facilitate osteo-integration.

Each of the embodiments described herein can incorporate or cooperate with sensing mechanisms adapted to provide loading information concerning the tissues being treated. Thus, it is contemplated that the various pressure sensing mechanisms available can be placed upon the devices of the present invention. Such sensors can be configured to provide information about the efficacy of the energy manipulating device of the present invention and whether adjustments are necessary. Similarly, sensors can be placed on anatomy to provide information regarding loads being placed on the tissues themselves.

Furthermore, it is contemplated that drugs can be delivered to the interventional site targeted for energy manipulation. In this regard, the entirety of the subject matter disclosed in U.S. Publication No. 2007/0053963 is hereby incorporated herein, by reference thereto.

While the present invention has been described with reference to the specific embodiments thereof, it should be understood b those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for treating an articulating anatomical joint, said method comprising:
attaching a first component of an assembly to a first anatomical member of the anatomical joint; and
attaching a second component of the assembly to a second anatomical member of the anatomical joint;
wherein a tension member joins said first and second components to absorb load between the first and second members of the anatomical joint, and wherein the tension in the tension member decreases as the anatomical joint moves from extension to flexion;
wherein said attaching the first and second components comprise positioning at locations so that the first and second components overlap and define a pivoting location at which the first and second components perform a scissoring action during movement of the anatomical joint.

2. The method of claim 1, wherein the tension member transiently absorbs the load.

3. The method of claim 1, further comprising permitting at least a limited amount of axial rotation between the first and second members of the anatomical joint.

4. The method of claim 1, wherein said tension member applies a force in a direction substantially opposite to directions of load applied by the first and second members of the anatomical joint toward one another.

5. The method of claim 1, wherein the anatomical joint is a knee joint, and the location is approximately the midpoint of a Blumensaat's line of a femur of the knee joint.

6. An implantable energy absorbing assembly for an anatomical joint comprising:
first and second components configured to be attached at first and second anatomical members of the anatomical joint, respectively;
a tension member configured to be implanted within a patient and connected between the first and second components to absorb energy and reduce load transfer through the joint;
wherein tension in said tension member applies a force to the joint in a direction of distraction of said joint when implanted in said patient;
wherein first and second components overlap and define a pivoting location at which the first and second components perform a scissoring action during movement of the anatomical joint between extended and flexed orientations of the joint.

7. The assembly of claim 6, wherein the tension member is configured to move from a tensioned position to an untensioned position during motion of the joint.

8. The assembly of claim 7, wherein:
the tensioned position is at zero degrees of flexion of the joint; and
the untensioned position is between 30 degrees and 90 degrees of flexion of the joint.

9. The assembly of claim 6, wherein the tension member and the first and second components are configured to be entirely outside of the joint capsule.

10. The assembly of claim 6, wherein the tension member is an elastomer member or a spring.

11. The method of claim 1, wherein the tension member is configured to move from a tensioned position to an untensioned position during motion of the joint.

12. The method of claim 11, wherein:
the joint is a knee;
the tensioned position is at zero degrees of flexion of the knee joint; and
the untensioned position is between 30 degrees and 90 degrees of flexion of the knee joint.

* * * * *